United States Patent
Wunderlich et al.

[11] Patent Number: 5,387,415
[45] Date of Patent: Feb. 7, 1995

[54] ALOE VERA JUICE CONTAINING PELLETS PROCESS FOR PRODUCTION THEREOF AND THE USE THEREOF AS PHARMACEUTICAL, COSMETIC AND PERORAL AGENTS

[75] Inventors: Jens-Christian Wunderlich, Heidelberg; Ursula Schick, Wiesloch; Jurgen Freidenreich, Schriesheim; Jurgen Werry, Ludwigshafen, all of Germany

[73] Assignee: Alfatec Pharma GmbH, Heidelberg, Germany

[21] Appl. No.: 876,876

[22] Filed: Apr. 30, 1992

[30] Foreign Application Priority Data

Jan. 17, 1992 [DE] Germany ............... 4201172

[51] Int. Cl.⁶ .................. A01N 65/00; A61K 9/20
[52] U.S. Cl. .................. 424/195.1; 424/451; 424/456; 424/464; 424/484; 424/485; 424/486; 424/487; 424/488; 424/492; 424/520
[58] Field of Search .............. 424/195.1, 520, 401, 424/408, 456, 492, 484, 485, 486, 487, 488, 451, 464

[56] References Cited

U.S. PATENT DOCUMENTS

| | | |
|---|---|---|
| 3,691,281 | 9/1972 | Battista ............... 424/195.1 |
| 4,446,131 | 5/1984 | Moughan ............ 424/195.1 |
| 4,470,202 | 9/1984 | Braxton et al. ............ 34/5 |
| 4,500,510 | 2/1985 | Goldstein ............ 424/195.1 |
| 4,994,265 | 2/1991 | White ............... 424/195.1 |
| 5,089,407 | 2/1992 | Baker et al. ............ 435/179 |

FOREIGN PATENT DOCUMENTS

| | | |
|---|---|---|
| 1293128 | 11/1989 | Japan . |
| 6907579 | 11/1970 | Netherlands ............ 424/195.1 |

Primary Examiner—Thurman K. Page
Assistant Examiner—Peter F. Kulkosky
Attorney, Agent, or Firm—Omri M. Behr; Matthew J. McDonald

[57] ABSTRACT

Aloe vera juice containing pellets are formed by a dispersion of aloe vera juice in a matrix, principally comprising a skeleton builder namely collagen, gelatin, fractionated gelatin, a collagen hydrolysate, gelatin derivative, plant proteins, or plant protein hydrolysates. They are shelf stable and their cosmetic as well as pharmacological properties are substantially unchanged in comparison to the native extracts. They may be produced by a simple process in which a solution of the skeleton former is mixed with aloe vera juice extract, the dispersion of the skeleton former and the aloe vera juice into a very cold inert fluid, suitably liquid nitrogen, to form the pellets and the thus formed pellets dried.

23 Claims, 1 Drawing Sheet

ALOE VERA JUICE CONTAINING PELLETS PROCESS FOR PRODUCTION THEREOF AND THE USE THEREOF AS PHARMACEUTICAL, COSMETIC AND PERORAL AGENTS

FIELD OF THE INVENTION

The present invention is directed to aloe vera juice containing molded particles in particular pellets, which are characterized by a dispersion of aloe vera juice in a matrix which comprises substantially of a skeleton former of a hydrophilic macromolecule.

The invention is further directed to a process for the preparation of such pellets as well as their pharmaceutical, peroral or cosmetic use.

BACKGROUND OF THE INVENTION

Aloe vera (Aloe Barbadensis Miller); Synonym: Aloe Vera Tournefort ex Linne, Aloe Vulgaris Lammarck) has, since ancient times, been known as a traditional folk medicine in those regions in which this plant, belonging to the family Liliaceae, grows wild.

Used topically the gel-like plant juice has, for example, the properties of accelerating wound healing, having antibiotic action or a softening effect on the skin.

With respect to internal use, aloe vera juice has been utilized in the treatment of stomach ailments and disturbances of the gastrointestinal tract. Furthermore, there are reports of anti-inflammatory properties.

The original knowledge led thereto that aloe vera is today planted in large plantations in Central, South and parts of North America. The juice contained in the leaves is extracted on location in a very work-intensive process and subsequently concentrated under the mildest available conditions. The concentration of the content material in the freshly obtained juice lies in the region of 0.3 to about 1%. The trade recognizes fresh aloe vera fillet, aqueous concentrate, as well as spray or freeze dried product. The quality differences in commercially available product depend substantially, with respect to stability and composition upon the production technology utilized.

Aqueous concentrates or juice from the leaves are today successfully utilized for skin problems (for example burns, occasioned by the action of heat, ultraviolet, or x-rays) scratches, wounds, stomach illnesses or periodontoses. It would appear that the pharmacological action requires the totality of all the components. At present, there are intensive researches into activity of the individual components.

Since heretofore, no undesirable side effects of aloe vera juice have been noted. For several years this natural product has been offered in creams, moisturizing emulsions, suntan lotions and for internal use.

Basic difficulties are present with respect to the storability or shelf life of the aqueous plant gel. The fluid product is, despite preservatives, heat and pH unstable, oxygen sensitive and furthermore, subject to microbial attack.

The transport of fresh aloe vera juice is difficult and expensive by reason of the large fluid volume—one is utilizing 90–99% water—and the known instabilities. Furthermore, prior to production steps, it is essential that the juice be kept cool. The production methods, which include the steps of initially washing the leaves, obtaining the fillet, homogenization, cleaning the fillet, concentration and drying can, by using an improper technique, lead to changes in the content of the components and bacterial contamination of the end product.

Aloe vera powder obtained by spray or freeze drying suffers from the danger of lumping, because of a low level cross-linkability, and thus may only be redissolved in cold water with considerable difficulty. Furthermore, spray dried products are hygroscopic which, in unsuitable storage, can easily lead to stickiness. Conventional products which dissolve readily in water often have solvating agents added thereto which is undesired in cosmetics.

It is therefore the task of the present invention to provide an unpreserved, shelf stable, concentrated, solid or semi-solid form of aloe vera juice which is readily redissolved without problems and whose pharmacological and cosmetic properties are preserved unchanged in comparison to the native plant juice.

SUMMARY OF THE INVENTION

This task is solved therein that aloe vera juice containing pellets are formed which are characterized by a dispersion of aloe vera juice in a matrix which comprises principally of a skeleton former of a hydrophilic macromolecule.

In particular, the invention makes available aloe vera juice containing molded particles, in particular pellets, which are characterized by a dispersion of aloe vera juice in a matrix which comprises principally hydrophilic macromolecules selected from the group consisting of collagen, gelatin, fractionated gelatin, collagen hydrolysate, gelatin derivatives, plant proteins, plant protein hydrolysates, elastin hydrolysates, as well as mixtures thereof.

Furthermore, the present invention makes available a process for the preparation of aloe vera juice containing molded particles, in particular pellets characterized thereby that:
a) a skeleton former of hydrophilic macromolecules selected from the group consisting of collagen, gelatin, fractionated gelatin, collagen hydrolysates, gelatin derivatives, plant proteins, plant protein hydrolysates and elastin hydrolysates are mixed with liquid aloe vera juice, and
b) the thus obtained mixture of skeleton former and liquid aloe vera juice is dropped into a very cold inert fluid whereby the pellets are formed and
c) the pellets are dried.

Generally speaking, in the literature one speaks of aloe vera juice, aloe vera gel and aloe vera extracts. In the sense of the present invention, the general concept of "aloe vera juice" is utilized to include native juice obtained directly from the leaf, filtered or cleaned juice, as well as redissolved juice from dry extract. For internal use, the complete leaf, leaf parts and blossoms in homogenized form may also be utilized. For special purposes, the individual components may also be suitable.

As hydrophilic molecules, there may be utilized collagen, gelatin, fractionated gelatin, collagen hydrolysate, gelatin derivatives, plant proteins, plant protein hydrolysates, elastin hydrolysates and combinations of the above-mentioned materials with each other.

The task is further solved by a process for the preparation of pellets containing aloe vera juice characterized thereby that the skeleton formers are mixed with fluid aloe vera juice, the formed pellets formed and the pellets subsequently dried.

The preferred embodiments of the invention are described and claimed in the subclaims.

The pellets of the present invention are rounded, molded, unitary particles having a grain size in the range of 0.2 to 12 min. Surprisingly, they are of high firmness having low friability. They are shelf stable, well dosable, and because of the special method of production, fall in the manner of free flowing product. They contain aloe vera (calculated on solid content) in the concentration of 0.1 to 98% (weight percent), preferably 0.1–60 wt. %.

Surprisingly, neither the type nor composition of the components of the aloe vera juice are altered by the pellets of the present invention. The aloe vera juice containing pellets can, in accordance with the mode of formation, be either lyophilisates or solid, suitably gel formed pellets.

The product of the present invention can be directly utilized for cosmetic as well as internal, that is to say, pharmaceutical uses.

For cosmetic uses in accordance with the present invention, it is particularly advantageous to utilize soluble collagen, gelatin, fractionated gelatin, elastin hydrolysate, collagen hydrolysate, plant proteins or other hydrolysates as carrier material for the molded particle.

Gelatin is a collagen containing material derived from scleroprotein which has different properties, depending on the mode of preparation. It consists substantially of four molecular weight fractions which influence the physicochemical properties in dependence upon the molecular weight and percentage proportion. The higher, for example, the proportion of microgel ($10^7$ to $10^8$ D), the higher is also the viscosity of the aqueous solution. Commercially available materials have up to 10%. The fraction of alpha gelatin and its oligomers ($9.5 \times 10^4/10^5$ through $10^6$ D) are determinative for the gel solidity and generally constitutes between 10 and 40 wt. %. Molecular weights under that of alpha gelatin are designated as peptides and in conventional gelatin qualities (low bloom) can constitute up to 80 wt. %.

Gelatin has a temperature and concentration dependent reversible sol/gel transformation property, which is dependent upon the molecular composition. The measure of the gel formation property of the gelatin is, in international usage, designated as the bloom number. Lower levels of commercial qualities begin at 50 bloom, high bloom varieties have a level of about 300 bloom.

Fractionated gelatins are a special type of gelatin and are obtained by special production techniques, for example ultrafiltration, from conventional gelatin. The composition can be varied, for example, by the removal of peptides (molecular weight less than $9.5 \times 10^4$ D) or by mixtures of individual fractions such as for example alpha chains, dimers and timer chains or microgels.

Collagen in native form is water insoluble. Through special production modes it is today possible to obtain collagen types which are soluble.

Gelatin derivatives are chemically altered gelatins for example succinylated gelatin which, for example, can be used as a plasma expander.

Under the term collagen hydrolysate there is understood a product obtained from collagen or gelatin by pressure or enzymatic hydrolysis, which no longer has the sol/gel transformation ability. Collagen hydrolysates are readily cold water soluble and the molecular weight composition may lie between a few hundred D and below $9.5 \times 10^4$ D.

These materials of biogenic origin shows themselves not only to be well tolerated by the skin but they are particularly suitable for incorporation in ointments, cremes and emulsions. Thereby, they demonstrate their particular ability to operate as emulsifiers and emulsion stabilizers. Thus for example, the addition of large amounts of skin irritating tensides (solvating agents) can be further reduced, which adds to the skin compatibility required by modern cosmetic technology. Gelatin and collagen hydrolysates are pharmaceutically recognized additives which are also preferentially utilized in the cosmetics industry.

Plant proteins and the hydrolysates thereof are newly developed properties, whose properties correspond to a very large extent to those of collagen hydrolysates. They are preferably obtained from wheat and soya and have molecular weight ranges of 200,000 to 300,000 D and from about 1,000 to about 10,000 D respectively.

By using plant proteins, plant protein hydrolysates, elastin hydrolysates for example those obtained from collagen hydrolysates (cold water soluble gelatins or gelatins with a maximum molecular weight distribution from a few hundred D to below $10^5$ D (Variant A) the carrier material of desired molded particle of the present invention upon lyophilization, surprisingly yields a highly porous and at the same time mechanically stable matrix.

Elastin hydrolysates are obtained enzymatically from elastin and consist of a single peptide chain. Because of their high proportion of non-polar amino acids, these can be utilized in lipophilic systems. Elastin hydrolysates have a molecular weight in the range of about 2000 to 3000 D and readily form films on the skin.

The rapid solution of the described matrix prescriptions is advantageous for preservative free instance cremes.

The recognized healing action of aloe vera juice for internal (health care) permits the pellets of the present invention to advantageously improve the form of preservative free instant preparation. If for example, aloe vera juice is cryopelletized with a rapidly dissolvable matrix, there are obtained shelf stable pellets which for example when filled in bags, can be dissolved in fruit juices, milk or other drinks within a few seconds. It is also advantageous to produce complete ready-made drinks with the products of the invention comprising aloe vera juice, a matrix mass of protein of biological origin (for example collagen hydrolysates, wheat proteins) and natural matrix builders, fruit juice extracts, honey and other natural components.

Where the pellets of the present invention are not in lyophilized form but rather in solid or semi-solid form, they can be advantageously built up from sol/gel forming hydrophilic macromolecules, for example gelatin or fractionated gelatin with a maximum molecular weight distribution above $10^5$ D, whereby the consistency depends directly from the type and concentration of the softening agent additive.

In particular, semi-hard pellets can be so provided in the matrix mass that after application they melt or dissolve. The skin friendly action of the natural products forming the matrix is thereby advantageous.

Hereinbelow the process of making the process of the present invention will be more closely described.

Further embodiments are set forth in the parallel United States applications for Letters Patent as set forth herein, whose disclosure is incorporated herein by reference. These parallel U.S. applications have been filed in the United States Patent and Trademark Office by the same inventors on the same day and are as follows:

Title: "Pellets Containing Peptides, Method of Making Same and Use Thereof", U.S. Ser. No. 07/876,865.

Title: "Means for Containing Active Substances Having a Shell of Hydrophilic Macromolecules, Active Substances and Process for Preparation Thereof", U.S. Ser. No. 07/876,864.

Title: "Pellets Containing Plant Extracts, Process of Making Same and Their Pharmaceutical Peroral or Cosmetic Use", U.S. Ser. No. 07/876,866.

Title: "Soft Gelatin Capsules", U.S. Ser. No. 07/876,863.

Title: "Peroral Dosage Form for Peptide Containing Medicaments, in Particular Insulin", U.S. Ser. No. 07/876,867.

Title: "Pellets Containing Dihydropyridine Derivatives Process for Production Thereof and Use as Rapid Action Dosage in Heart and Circulatory Diseases", U.S. Ser. No. 07/876,877.

In the simplest case, the aloe vera juice containing pellets can be produced in the following three process steps:

a) The skeleton former of hydrophilic macromolecules is mixed with liquid aloe vera juice.

b) The mixture of the skeleton former and the liquid aloe vera juice is dropped into a exceedingly cold inert fluid and thus forms pellets.

c) The thus obtained pellets are dried.

In the procedure step described in a) above, the dropable mass is formed principally out of a hydrophilic molecule to form the skeleton builder, particularly selected from the group consisting of plant protein, plant protein hydrolysates, collagen, gelatin, fractionated gelatin, elastin hydrolysates, collagen hydrolysates, gelatin derivatives or mixtures of the above-identified materials and the aloe vera juice.

Thereafter, either freshly obtained or already concentrated liquid aloe vera juice is dissolved in the desired skeleton builder in particular plant proteins, plant protein hydrolysates, collagen, gelatins, fractionated gelatins, gelatin derivatives, collagen hydrolysates, or elastin hydrolysate, wherein the type and amount of the utilized skeleton former and similarly, the addition of further inert ingredients are determined by the later utilization of the pellets. The concentration of the carrier material can lie suitably from 0.5 to 60% (wt. for wt.), suitably 0.5 to 30% (relative to the total mass to be worked). The use of warming in the temperature range of about 30° C. to about 45° C. can, where gelatin is used, be employed in order to convert this into the sol form.

For cosmetic, internal, suitably pharmaceutical use, there may further be added to this ground mass, inert ingredients and carrier materials, for example additional skeleton builders which are described in more detail hereinbelow, softening agents such as for example glycerols or sorbitol, fillers for example lactose, dispersants for example disodium phosphate, pH adjusters for example disodium citrate, emulsifiers such as for example lecithin, stabilizers for example ascorbic acid, cosolvents for example polyethylene glycol, natural colorants for example carotinoides, odorants or taste adjusters for example fruit concentrates.

In a further embodiment of the invention, the residual moisture content of the dried pellets and thus their consistency as solid, semi-solid or gel forms can be adjusted by the addition of softening agents, for example glycerol or sorbitol, in the range of 1–50%, based on the mass to be worked.

After formation the pellets can, without intermediate storage or previous drying be directly converted into creams or hydrogel bases.

Furthermore, it can be technologically advantageous to add other skeleton forming substances to the prescription mass, in addition to the skeleton formers of the previously mentioned hydrophilic molecules.

As additional skeleton formers there can be utilized albumin, agar, gum arabic, pectin, tragacanth, xanthan, natural and modified starches, dextran, dextrins, maltodextrin, chitosan, alginates, cellulose derivatives, sugar or saccharose, glycine, lactose, polyvinylpyrrolidone, mannitol and combinations thereof.

In yet a further embodiment, supplements of material selected from this group can be utilized to modify the physical or chemical properties of the matrix, for example the viscosity, the mechanical solidity or the solubility properties of the polymeric skeleton in dependence upon their use. Thus, for example by addition of dextrans, modified starches, sugars and in particular mannitol, pellets may be prepared in accordance with the present invention which spontaneously and completely dissolve in cold water.

Furthermore, it may be desirable for cosmetic purposes, to add lipophilic components such as for example phospholipids, to produce liposomes to the described matrix masses.

In exceptional cases the component materials of aloe vera itself, in particular after concentration, may be utilized as skeleton formers for the production of pellets in accordance with the present invention.

In the step b) of the procedure the described matrix mass is rounded (molded) and shock frozen by dropping into in a dropping bath in the region of −70° C. to −270° C., suitably −100° C. to −220° C. by dropping thereinto. As exceedingly cold and inert fluids there is suitably used liquid nitrogen which does not alter the content of the pellets. In the exceedingly cold fluid there are formed round molded particles (pellets) which, after drying, form a mechanically stable matrix. The mold formation proceeds via a suitable dosage system. Thus, each discrete drop on the one hand during the free fall and on the other hand in the dropping bath, because of the gas surround formed by the surface tension between the system and the gas, takes on a spherical shape before it freezes entirely. Just this rapid but yet modifiable and controllable freezing fixes the particular condition of the system instantaneously, that is to say, none of the content materials of the aloe vera juice can diffuse into the surrounding medium, dissolved components can no longer crystallize out, suspensions can no longer sediment, thermally sensitive or moisture sensitive components of the juice are cryoconserved, the carrier skeleton cannot shrink together anymore and so on. The production process utilizing an inert gas has therefore no negative influences or cannot bring about any change in the product. Of particular advantage is thus the maintenance of the desired properties. Furthermore, the process operates without solvents, does not harm the environment and can be carried out under sterile conditions.

As a dosage system, there may be used any arrangement which provides discrete, equal drops of predetermined size, that is to say, pipette-type dropping arrangements or suitable spray or dust jets, in conjunction with dosage pumps.

Furthermore, one may use dosage arrangements with single substance jets in the process of the present invention, which eject the drops in a timed or intermittent manner.

A further preferred embodiment of the present invention comprises a procedure utilizing the Cryopel® dosage system developed by Messer Griesheim GmbH (based on DE OS 37 11 69). In combination with a drop freezing arrangement, the Cryopel® apparatus makes the scaling up of the process of the present invention particularly simple. This arrangement which can be driven with liquid nitrogen distinguishes itself particularly well economically. This arrangement is particularly useful for sterile proceedings. Continual production methods with little maintenance and cleaning requirements makes possible the economic practice of the process invention on an industrial scale.

BRIEF DESCRIPTION OF THE DRAWINGS

There is shown:

FIG. 1 is a schematic representation of the Cryopel® process developed by Messer Griesheim GmbH. The matrix mass formed in accordance with the present invention is dropped, via a heated provision arrangement 1 via calibrated jets into the fluid nitrogen bath 3 in drops at about −196° C. and formed under simultaneous shock freezing into round pellets. The frozen products are removed over arrangement 5 via continuously running transport band 2. The dosing of the liquid nitrogen is carried out via line 7 and the thus produced nitrogen gas is expelled via line 6. Insulation 4 encompasses the entire system.

In FIG. 2 is a schematic representation of the process wherein the cold matrix mass, which may be heated to a maximum of 50° C. is lead via a controllable dosage pump 8 over line 9 in a continuous manner through the heatable dropping jet 10 and dropped into the insulated bath 11 containing liquid nitrogen 12. The shock frozen pellets are removed batchwise. This arrangement permits the processing of highly viscous masses.

Figure 1:
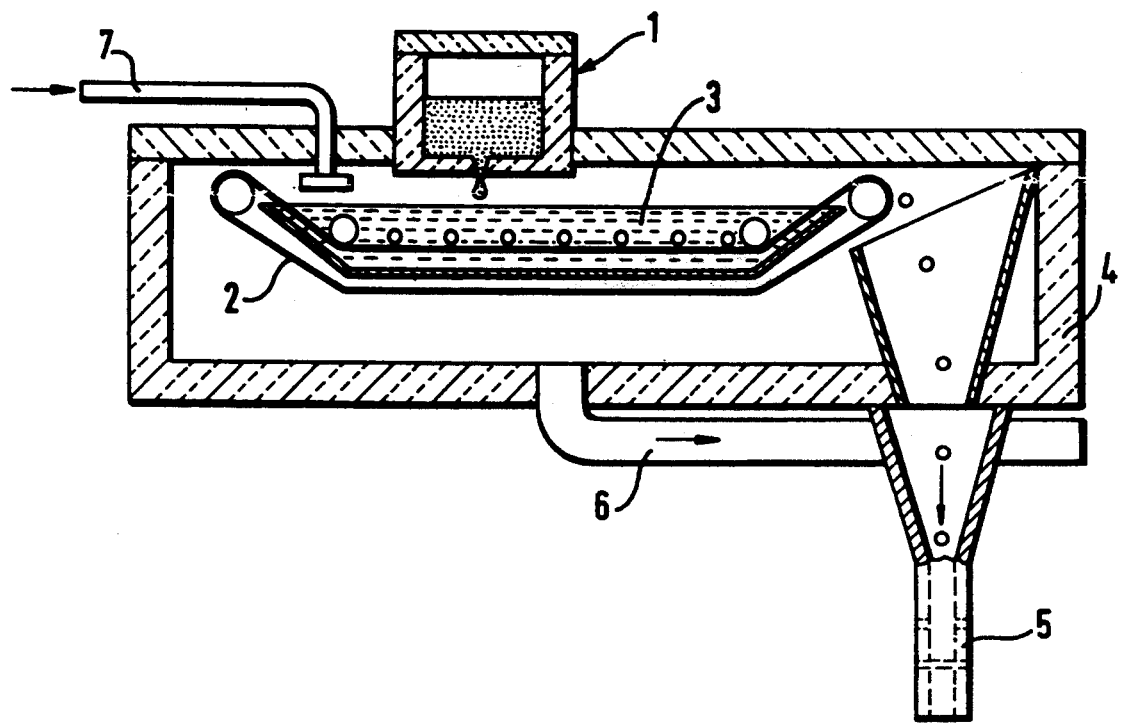
FIG. 1—A schematic representation in cross sectional elevation of an arrangement for carrying out the process of the present invention.

Where the system to be processed is not sufficiently capable of flowing or forming drops one can, for example, add additional amounts of water of between 1 and 10 wt. %, the processing temperature may be raised or pressure may be utilized in the dosage step. In the contrary case, for example the system has too low a viscosity, analogously, reduced pressure may be utilized. This mode of proceeding provides a regular formation as well as separation of individual drops.

The processing temperature may be varied across a wide range. Preferably this should lie under 50° C., in the case of aloe vera, to avoid thermal deterioration of the components.

Thus, for example utilizing the Cryopel® dosing mass, one can readily operate in the viscosity area of $1 \times 10^{-3}$ to 12.5 Pa seconds without any difficulty.

Additional very cold fluids which may be utilized for the process of the present invention include for example liquid inert gases for example argon.

In dependence upon the dosage system chosen a grain size compatibility of over 70% can be achieved which can be increased through classification.

The segment removed by classification can again be recycled into liquid state and again be pelleted so that a loss-free mode of proceeding is given.

In dependence upon the chosen dosage system, it is possible to obtain a grain uniformity of over 70% which can additionally be improved by classification. The particles separated by classification can be recycled into the fluid state and again repelleted. Thus, there is provided a waste-free procedure.

In one embodiment that is described in step c) of the above process, the pellets can be dried, there being two modifications thereof.

Variant A

The pellets frozen at −196° C. are transferred into a freeze drying arrangement. There are chosen temperatures of about 15° C. below the sublimation point of water at pressure of 0.1 Pa to 103 Pa (0.001 to 1.03 mbar). The drying arrangement which is carried out in a conventional freeze drying apparatus (condenser temperature −40° C.) at a temperature of 25° C. and 33 Pa (0.33 mbar) proceeds in the primary drying step in the sublimation of the water amorphously frozen in the shock freezing out of the matrix, the secondary drying (desorption) leads to an end product with a highly porous network. Such pellets are, compared to conventionally freeze dried products, particularly readily soluble and are preferred for the development of instant preparations.

Variant B

The frozen pellets are permitted to thaw and are conventionally dried. Here, it is advantageous for the acceleration of the drying process and the maintenance of a low temperature, to operate under vacuum, 3000 to 5000 Pa (30 to 50 mbar). Drying temperatures of up to 50° C. may be chosen, whereas the temperature of pellet matrix during the drying stage, because of the evaporation enthalpy of the fluid does not raise above 30° C.

For conventionally dried pellets (Variant B) it is necessary to utilize gel forming substances for the matrix which are capable of forming drops in sol form and, after cryopelletization and the melting of the gel, are stable after drying. The addition of softeners assists in the maintenance of uniformly round molded particles. The thus produced pellets show themselves to be economically formable and may be utilized both in cosmetic as well as pharmaceutical fields.

Compared to the known procedures of the art, the process of the present invention requires very little servicing and can be very economically carried out. This easily practiced technique makes it possible to directly process and fresh aloe vera juice in the country of origin as well.

The pellets of the present invention are suitable for peroral and cosmetic purposes as well as for pharmaceutical purposes.

As cosmetic uses there may be mentioned for example:

Formation of creams, instant creams, moisturizing emulsions, sun protection substances, substances against sunburn, shampoos, toothpaste, soaps, bath additives, and facial waters.

Direct use of the pellets for the preparation of face masks, powders, and the like.

Formation of plasters for wounds and wound powders.

Furthermore, the particles of the present invention can also be used as oral or peroral dosage forms.

Use in cosmetics in dissolved or semi-solid form.

Use in cosmetics in combination with other active substances.

Pharmaceutical uses are for example:

Formation of ointments, creams, gels, for treatment of wounds for burns scrapes, etc.

As substrates for the formation of tablets, dragees, etc.

The pellets are exceedingly suitable for direct tableting. Because of the high readily attainable grain size predictability, no dosage problems arise.

Pellets can be directly charged into hard gelatin capsules or into bags.

Filled into bags, the pellets can be utilized for the preparation of health care drinkable solutions (instant preparation). With the utilization of plant proteins, plant protein hydrolysates, collagen hydrolysates or gelatin with a maximum molecular weight distribution of from a few hundred D to less than $10^{-5}$ D, the pellets of the present invention dissolve in water at ambient temperature in a few seconds. There are also possible mixtures of different plant extracts or with other active substances in this form.

Because of the considerable variability of the prescription masses and the described formation procedures, the properties of the pellets of the present invention can be very readily provided for the desired utilization purpose.

Special matrix formation enables the direct utilization of pellets in solid or half-solid forms whereby the solution results during dosing.

By variation of the bloom level of the gelatin used in the present invention, only the properties, as for example the control of the solution speed of the pellets of the present invention, but also the desired viscosity of the thus produced aqueous solution, can be directed in accordance with the ultimate use.

The invention can be illustrated by the following examples.

EXAMPLE 1

150 g. of Collagen hydrolysate (mean molecular weight: 3,000 g/mol.)

3000 g. of Aloe vera juice, solid content 0.6% (wt/wt)

The freshly obtained filets of aloe vera leaves are homogenized, cleaned and filtered, the collagen hydrolysate is dissolved in the thus obtained cooled aloe vera juice. Subsequently, the solution is dropped into a dropping bath containing liquid nitrogen at −196° C. via the Cryopel® dosing arrangement and the pellets thus formed.

The shock frozen round molded particles are dried in a freeze dryer at a primary drying at −50° C. and 5 Pa (0.05 mbar) and a second drying at 22° C.

There are thus obtained pellets of a diameter of 4 mm and an aloe vera content of 10.7% (wt/wt dry substance). By classification the grain size exactness is 78%.

The pellets are completely soluble in water at ambient temperature within 20 seconds.

EXAMPLE 2

100 g. Collagen hydrolysate (mean molecular weight: 3,000 g/mol.)
50 g. Mannitol
50 g. Wheat protein hydrolysate (molecular weight <5.000 g/mol.)
2000 g. Aloe vera juice (solid content concentration 0.6%)

In the aloe vera juice obtained in accordance with Example 1, the collagen hydrolysate, the wheat protein hydrolysate and the mannitol are dissolved in the cold and as in Example 1, are pelletized. The thus obtained pellets have a diameter of 3 mm and have an aloe vera solid component of 5.7% (wt/wt). These pellets can be dissolved in orange or maracuja juice to provide a drinkable solution.

EXAMPLE 3

200 g. Collagen hydrolysate (mean molecular weight: 3,000 g/mol.)
4000 g. Aloe vera juice (10 times concentrate)

The aloe vera juice obtained in accordance with Example 1 is concentrated to a ten-fold concentrate in a one-step vacuum evaporator at 5,000 Pa (50 mbar) and 40° C. The collagen hydrolysate is dissolved in the juice and after rapid pasteurization, lyophilized pellets are produced. There are thus obtained round molded particles with a diameter of 4.5 mm of an aloe vera solid material content of 54.5% (wt/wt).

The pellets dissolve in water at room temperature within 40 seconds.

5. g. of these pellets in 100 ml. of sterile water yield an effective instant prescription against sunburn.

EXAMPLE 4

Incorporation of pellets of the present invention in a night cream.

a) Pellet Formation 300 g. Collagen hydrolysate (mean molecular weight: 13,000–18,000 g/mol.)
4000 g. Aloe vera juice (solid concentration) 0.6%.

Lyophilized pellets as described in Example 1 are prepared which have a solid aloe vera content of 7.4% (wt/wt/).

b) Prescription for the Night Cream Fatty Phase:
200 g. Tegomuls 90S
750 g. Avocado Oil Aqueous Phase:
200 g. Native collagen (3% solution molecular weight: 300,000 g/mol.)
30 g. elastin
32 g. Aloe vera pellets as per a)
3000 g. Freshly distilled water The fat phase is melted at 70° C. The water is equally heated to 70° C. and the elastin dissolved therein. The thus obtained aqueous solution is homogenized in the fat phase, the cream base is cooled to 35° C. The aloe vera pellets are dissolved in the cold collagen solution and dispersed in the homogenized creme base.

EXAMPLE 5

400 g. Commercial gelatin (170 bloom)
300 g. Glycerin (85%)
1300 g. Aloe vera juice (solid material concentration 0.5% (wt/wt)

The gelatin powder is added to freshly obtained homogenized aloe vera juice and preswollen therein for ca 45 minutes. Subsequently, the mixture is totally dissolved at 45° C. and the glycerine homogeneously mixed therewith.

Figure 2:
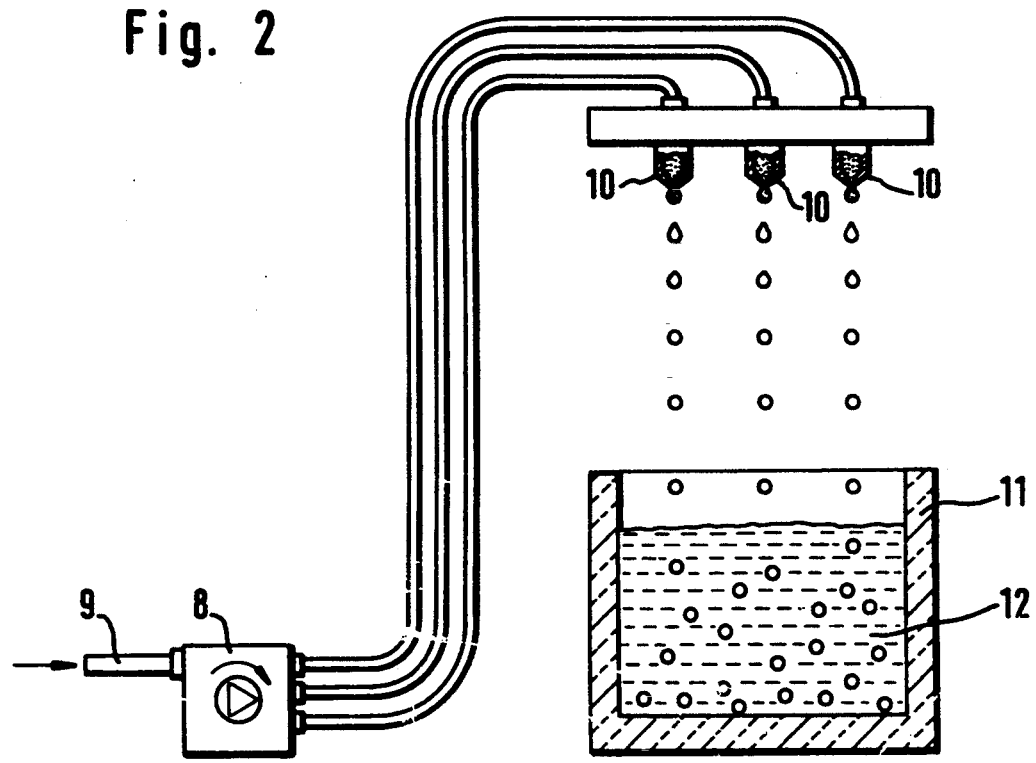
FIG. 2—A further arrangement for carrying out the process of the present invention in schematic illustration.

Subsequently, via the apparatus set forth in FIG. 2, the solution at 40° C. is dosed to the liquid nitrogen containing bath via a pump and the pellets thus formed. The deep frozen round molded particles are thawed and dried at a temperature rising from 25° C. to 40° C. The pellets have a residual moisture content of 10% and are shelf stable.

The thus obtained pellets can be incorporated into commercial hydrogel (polyacrylate gel). After 10 to 15 minutes, the pellets swell in the hydrogel to approximately twice their original size and form a readily meltable molded particle which will dissolve after application to the skin.

Alternatively, the pellets can be incorporated in the hydrogel directly without drying and without intermediate storage.

We claim:

1. Aloe vera juice containing dried cryopellets comprising aloe vera juice the activity and amount whereof is essentially undiminished by the cryopelleting dispersed in a matrix comprising substantially at least 50% w/w of a skeleton forming water soluble hydrophilic macromolecular material selected from the group consisting of collagen, gelatin, fractionated gelatin, collagen hydrolysates, succinylated gelatin, plant proteins, plant protein hydrolysates, elastin hydrolysates and mixtures thereof.

2. Dried cryopellets in accordance with claim 1 further comprising at least one additional skeleton forming hydrophilic material selected from the group consisting of albumin, agar agar, gum arabic, pectins, tragacanth, xanthan, natural and modified starches, dextrans, dextrins, maltodextrin, chitosan, alginates, cellulose derivatives, dextran, sugar, glycine, lactose, mannitol and polyvinylpyrrolidone.

3. Dried cryopellets in accordance with claim 1 wherein said matrix further comprises pharmaceutically acceptable inactive ingredients or carrier material.

4. Dried cryopellets in accordance with claim 1 having a content of aloe vera juice of 0.1 to 98 wt. % (calculated as a dry substance).

5. Dried cryopellets in accordance with claim 1 having a particle diameter of 0.2–12 mm.

6. Dried cryopellets in accordance with claim 1 existing as lyophilisates.

7. Dried cryopellets in accordance with claim 1 which are rapidly dissolvable in aqueous media and said matrix comprises substantially of a member of the group consisting of a plant protein, plant protein hydrolysate, collagen hydrolysate, cold water soluble succinylated gelatin or gelatin the major portion whereof having a molecular weight under $10^5$ D.

8. Dried cryopellets in accordance with claim 1 wherein said matrix comprises as softeners, glycerin or sorbitol of between 1–50 wt. % relative to the total mass of the dried cryopellet.

9. Dried cryopellets in accordance with claim 8 existing in solid or semisolid or gel-like form.

10. Dried cryopellets in accordance with claim 8 comprising a gelatin the major portion whereof having a molecular weight above $10^5$ D, as a sol/gel former.

11. Process for the preparation of aloe vera juice containing dried cryopellets having a matrix the activity and amount whereof is essentially undiminished by the cryopelleting comprising the steps of:
  a) mixing, with aloe vera juice, a skeleton forming macromolecular material selected from the group consisting of collagen, gelatin, fractionated gelatin, collagen hydrolysate, succinylated gelatin, plant proteins, plant protein hydrolysates, elastin hydrolysates as well as mixtures thereof, said material comprising at least 50% by weight of said matrix;
  b) forming drops of the thus obtained mixture of macromolecular material and plant extract and dropping them into an exceedingly cold inert fluid at a temperature of between −70° and −270° C. whereby the cryopellets are molded, and
  c) drying said cryopellets.

12. Process according to claim 11 wherein the cold fluid is liquid nitrogen.

13. Process according to claim 11 wherein said drops are of equal predetermined form created by means of a dosing system capable of creating same.

14. Process wherein the pellets of step of claim 11 are directly incorporated into a creme or hydrogel base.

15. Process according to claim 11 wherein the molded particles are freeze dried in step c).

16. Process according to claim 11 wherein, to the mixture of macromolecular material and aloe vera juice there is added at least one additional skeleton forming hydrophilic material selected from the group consisting albumin, agar agar, gum arabic, pectins, tragacanth, xanthane, natural and modified starches, dextranes, dextrins, maltodextrin, chitosan, alginates, cellulose derivatives, dextran, sugar, glycine, lactose, mannitol, and polyvinylpyrrolidone.

17. Process according to claim 11 wherein, to the mixture of macromolecular material and aloe vera juice there are added as softeners, glycerin, sorbitol or mixtures thereof comprising 1 to 50 wt. % relative to the entire mass of the dried cryopellet.

18. Process according to claim 11 wherein the cryopellets are dried at a maximum of 50° C.

19. Process according to claim 11 wherein, as macromolecular materials, gelatins the major portion whereof having a molecular weight above $10^5$ D are mixed with the liquid aloe vera juice at a maximum temperature of 40° C.

20. A pharmaceutical preparation containing the dried cryopellets of claim 1.

21. A cosmetic preparation containing the dried cryopellets of claim 1.

22. A food preparation for health care containing the dried cryopellets of claim 1.

23. Aloe vera juice containing dried cryopellets comprising aloe vera juice dispersed in a matrix at least 50% w/w whereof comprising substantially of skeleton forming hydrophilic macromolecular material selected from the group consisting of collagen, gelatin, fractionated gelatin, collagen hydrolysates, succinylated gelatin, plant proteins, plant protein hydrolysates, elastin hydrolysates and mixtures thereof.

* * * * *